United States Patent [19]

Lhonoré et al.

[11] Patent Number: 4,505,879

[45] Date of Patent: Mar. 19, 1985

[54] REACTOR FOR NITRATION OF HYDROCARBONS IN THE GASEOUS PHASE UNDER PRESSURE

[75] Inventors: Pierre Lhonoré, Douai; Jacques Quibel, Maisons Lafitte; Bernard Jacquinot, Douai; Yvon Jestin, Rueil Malmaison; Robert Pelletier, Paris, all of France

[73] Assignee: Societe Chimique de la Grande Paroisse, Azote et Produits Chimiques, Paris, France

[21] Appl. No.: 278,004

[22] Filed: Jul. 6, 1981

Related U.S. Application Data

[63] Continuation-in-part of Ser. No. 131,004, Mar. 17, 1980, abandoned.

[30] Foreign Application Priority Data

Mar. 28, 1979 [FR] France ................................ 79 07840

[51] Int. Cl.³ .................... B01J 12/00; B01J 19/24; B01J 19/26
[52] U.S. Cl. ........................ 422/197; 137/561 A; 422/205; 422/224; 422/241
[58] Field of Search ............. 422/196, 197, 202, 224, 422/312, 205, 208, 240, 241; 568/947; 366/336; 137/561 A

[56] References Cited

U.S. PATENT DOCUMENTS

| | | | |
|---|---|---|---|
| 2,511,454 | 6/1950 | Bishop et al. | 568/947 |
| 2,512,587 | 6/1950 | Stengel | 568/947 |
| 2,638,407 | 5/1953 | Steeves | 422/197 |
| 2,878,108 | 3/1959 | Chandler | 422/205 |
| 2,986,454 | 5/1961 | Jewett | 422/197 |
| 3,482,948 | 12/1969 | Miegel | 422/197 |
| 3,572,999 | 3/1971 | Sato | 422/197 |
| 3,671,198 | 6/1972 | Wallace | 422/197 |
| 3,723,391 | 3/1973 | Beer et al. | 422/202 |
| 3,795,259 | 3/1974 | Brandin et al. | 137/561 A |
| 3,881,701 | 5/1975 | Schoenman et al. | 422/224 |
| 3,929,421 | 12/1975 | Werges | 422/197 |
| 4,173,615 | 11/1979 | Otsuka et al. | 422/197 |
| 4,183,897 | 1/1980 | Lanteri | 422/197 |
| 4,361,407 | 11/1982 | Pellegrini | 422/224 |

FOREIGN PATENT DOCUMENTS

1037438 8/1958 Fed. Rep. of Germany .
156264 1/1921 United Kingdom .

OTHER PUBLICATIONS

Perry; "Chemical Engineers' Handbook"; 4th Ed.; pp. 23-12 & 23-48; 1963.

Primary Examiner—Bradley Garris
Attorney, Agent, or Firm—Browdy and Neimark

[57] ABSTRACT

A reactor for nitration of saturated hydrocarbons having less than five carbon atoms, alone or in admixture, in the gaseous phase under pressure is made up of a reaction enclosure, in which a tube or pipe bank is in contact with a heated fluid of high heat-exchange capacity. The inside perimeter of the tubes does not exceed 800 mm, and if circular not in excess of 250 mm, and the ratio of the surface of the tube bank, in contact with the reaction medium, to the volume of the reaction enclosure is 1:1 to 3:1.

The reactor apparatus further includes a mechanical means to uniformly distribute the delivery of reaction medium gases to the various tubes of the bank so that the load difference between the most loaded tube and that of the least loaded tube is equal to 10% at the most.

The reactor also includes a tube bank injector which feeds the tube bank to assure homogeneous mixing of all the reaction fluids in the tube bank.

4 Claims, 6 Drawing Figures

REACTOR FOR NITRATION OF HYDROCARBONS IN THE GASEOUS PHASE UNDER PRESSURE

CROSS-REFERENCE TO THE RELATED APPLICATIONS

This application is a continuation-in-part of Ser. No. 131,004 filed Mar. 17, 1980, now abandoned.

FIELD OF THE INVENTION

This invention relates to a reactor for nitration of hydrocarbons in the gaseous phase under pressure.

BACKGROUND OF THE INVENTION

Various processes for the nitration of hydrocarbons have already been proposed. Of particular interest are processes for the nitration of propane, ethane and mixtures of these hydrocarbons. LHonore et al., U.S. Pat. No. 3,780,115, describes nitration of propane with nitrogen peroxide in the presence of oxygen, introduced in the form of air, under a pressure of 8 to 14 bars and at introduction temperatures of the reactants in the reaction zone on the order of 200° to 240° C.

Copending application Ser. No. 25,594, of Mar. 30, 1979, now U.S. Pat. No. 4,260,838 relates to nitration of a mixture containing a substantial amount of propane. The reaction temperature and pressure, contact time and quantitative ratios among the nitrating agent, the mixture to be nitrated and the oxygenated gas are selected so that the nitration reaction is performed in the homogeneous gaseous phase. The mixture to be nitrated contains propane and one or more other alkanes having up to five carbon atoms in the molecule.

The conditions for nitration of ethane are the object of copending Ser. No. 94,153 of Nov. 14, 1979 now U.S. Pat. No. 4,313,010. According to this process the quantitative ratios of the various constituents of the reaction mixture, the reaction contact time and the reaction temperatures and pressures are selected and controlled so that nitration of the ethane takes place in a homogeneous gaseous phase, and as a function of the range of nitroparaffins expected to be obtained.

As in the previous processes for nitrating propane or propane base mixtures, the nitration reaction can be performed in the presence of an active agent carrying an easily transferable NO or $NO_2$ group, such as 2-nitropropane or nitroethane, alone or in mixture, possibly recycled reaction product. These nitrations are also advantageously performed in the presence of a gas, inert in the reaction (hereinafter an "inert gas"), selected from nitrogen, carbon monoxide, carbon dioxide, hydrogen, methane, argon or a mixture of any of these gases.

For all these processes, the highest yields are obtained only by working with a gradual and regular heat regime, i.e. by controlling the temperature curve inside the reaction zone; this curve must be smooth, i.e. have a regular growth without inflection points. Such a heat regime can be obtained only by avoiding any racing of the reaction and the appearance of high temperatures at certan points of the reaction zone.

OBJECTS AND SUMMARY OF THE INVENTION

There has now been found a type of reactor that can be used in all nitrations of saturated hydrocarbons having less than five carbon atoms, in the gaseous phase under pressure. This reactor by its structure makes it possible to obtain a heat regime with regular progression during the nitration reaction, i.e. the evolution of the reaction temperature curve is continuous and progressive, without sudden acceleration of the reaction rate and without appearance of temperature peaks at various spots of the reaction zone.

It is therefore an object of the invention to construct the reactor of a metal which will resist corrosion by contact with a nitrating agent. It is also an object of the invention to provide a reactor having efficient heat exchange characteristics and possessing a good response to the temperature elevation curve during the reaction.

It is a further object of the invention to provide a reactor wherein the difference in temperature between the hottest point on the tube or pipe bank of the reactor does not exceed about 20° C.

It is another object of the invention to construct the reactor of a metal which can resist rupture due to pressures in the tubes or pipes, which carry the heating fluids, that can reach 100 bars at the ambient operating temperatures of the nitration reaction.

It is a further object to construct the reactor and the mixture-distributor unit of a metal that will permit higher yields of the nitration reactions while concurrent oxidation reactions are kept to a minimum.

It is a still further object to provide a reactor consisting of pipes in which the reaction mixture is very evenly distributed and homogeneously mixed.

DETAILED DESCRIPTION OF PREFERRED EMBODIMENTS

Figure 1:
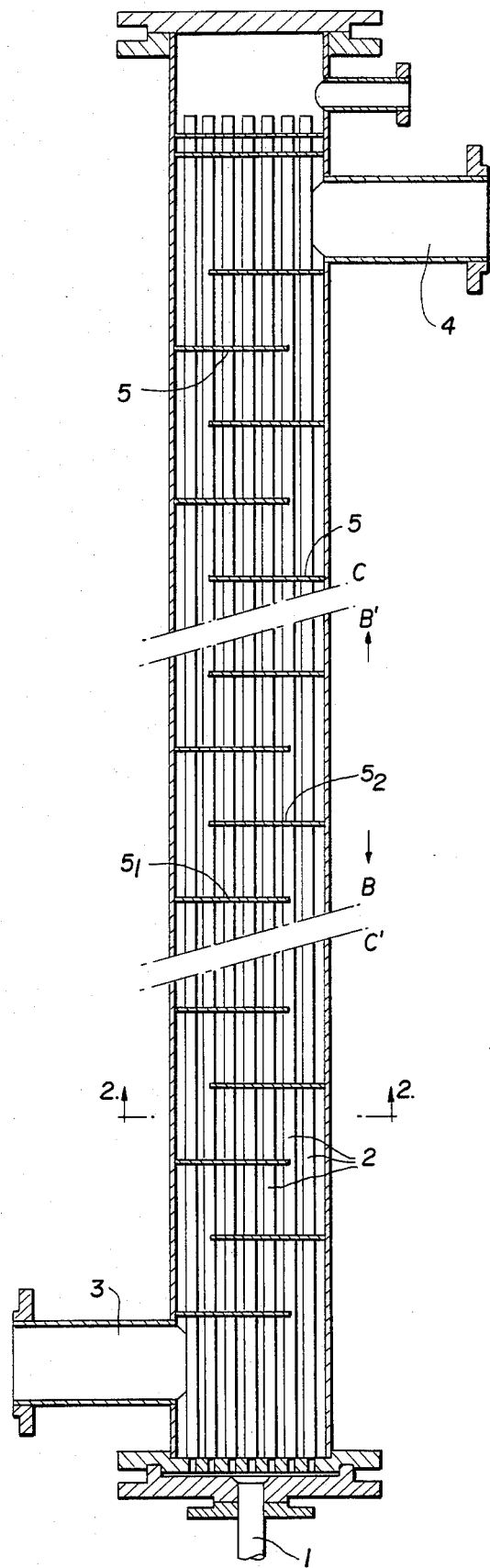
FIG. 1 shows a vertical section of the prototype reactor of Example 1, infra.

The reactor, according to the invention, is made up of a reaction enclosure, in which a tube or pipe bank is in contact with a heat-carrying fluid, with a high heat exchange capacity. The heat-carrying fluid which carries the heat of the nitration reaction or that necessary for heating the reactants can be vapor, e.g. steam, a bath of molten salts or any suitable heat-carrying fluid. The heat-carrying fluid is selected so that the temperature of the outside skin of the tubes is kept constant with only about 20° C. difference between the hottest point and the coldest point of the tubes.

Most often, the tube bank is immersed in the heat carrying fluid and the nitration reaction takes place inside the tubes. But it is possible, within the scope of the invention, to envisage nitration taking place outside the tubes, the heat-carrying fluid being housed inside the tubes.

The size of the tubes of the bank plays a role in the regular increase of the temperature during the progress of the reaction. The shape of the cross section of the tubes makes no difference if it allows a good flow of the gaseous fluids, either circular or oval, provided the inside perimeter of the tubes of the bank is at most equal to 800 millimeters; the inside diameter of the tubes of circular section is at most equal to 250 millimeters.

Further, it has been noted that the judicious choice of the ratio between the surface of the tube bank, in contact with the reaction medium, and the volume of the reaction enclosure has a favorable influence on the smooth and regular increase of the temperature during the reaction. A ratio range giving this favorable result is 0.1 to 20.1, preferably 0.5 to 5:1, and in particular 1 to 3:1.

Obtaining nitration products with good yields is also related to the regular maintenance of contact times in all the tubes of the bank; moreover, this is valid only with comparable deliveries (throughputs) in the various tubes of the bank. The regular distribution of the delivery in the various tubes of the bank can be assured by a mechanical means with which the reactor is equipped. It is advantageous to distribute the delivery so that the maximal load difference between the most loaded tube and the least loaded tube does not exceed 10%.

The reaction is fed by the action of an injector which assures a homogeneous mixing of all the reaction fluids.

The tube bank is made of a metal which resists corrosion by chemical action with the nitrating agent: nitric acid, nitrogen peroxide, alone or in mixture, or any other agent carrying an easily transferable NO or $NO_2$ group; and the metallic coupling formed with the metal of the injector is critically selected so that it does not cause ignition of the reaction fluids at the input of the reaction chamber.

The nitration reactor described above provides excellent performance in all types of nitrations of hydrocarbons in the gaseous phase under pressure, particularly saturated hydrocarbons of less than five carbons, in particular ethane and propane and their mixtures, possible in the presence of oxygen, recycling products, adjuvants and inert gases. The processes described in the disclosures, cited above, are advantageously used in the present reaction.

The reactor, made up of a bank of pipes, has from the structural viewpoint three types of characteristics.

The first characteristic deals with the section and shape of the pipes; the ratio between the inside surface of the pipes and the inside volume of the bank is an important factor to obtain a good flow of the reaction gases and good heat exchange. This ratio is S/V and defines the thickness of the gas stream.

The second characteristic relates to the irregular arrangement of the baffles on the inside of the pipe bank, of the segmented (according to the figures) disk or ring type. The distance between the two baffles is minimal in the reaction zone. This arrangement is intended to assure the best heat exchanges between the heat-carrying fluid and the reaction gases. This arrangement is intended to reduce as much as possible sites of low heat transfer in the zone where the reaction occurs and in the zone where the effluents are cooled.

According to the third characteristic, the reactor is equipped with a reaction gas mixer combining the technology of dynamic and static mixing. The distributor unit, all or part of its surface being in contact with the heat-carrying fluid, has the role of distributing the gases in the various pipes and is characterized by a succession of widenings and narrowings of the sections for passage of the reaction gases, in particular a considerable narrowing (calibrated orifice) of the passage section at right angles with each pipe of the bank (at the base of each pipe in the axis of the pipe, see FIG. 3). This restriction of the gas passage makes possible a better distribution of the gases between each pipe so that the load difference between the most loaded tube and that of the least loaded tube is equal to 10% at the most. On the other hand, the reactor is performing only to the extent that the heat exchanges are efficient and is characterized by parameters that define the features of the process, namely, the values of the ratios Q/US and Q'/US.

Q designates the heat released by the reaction, Q' designates the total heat exchanged with the heat-carrying fluid, i.e. the sum of the total heat given up to the mixture of reaction gases and the heat given up to the heat carrier salt during the reaction and cooling of the gases. U designates the over-all heat exchange coefficient and S the available exchange surface.

The choice of the ratios Q/US and Q'/US can be selected based on process features which characterize the mode of circulation of the heat-carrying fluid to the outside of the pipe bank.

The quality of the nitration reaction performed from a mixture of suitable composition (hydrocarbon, oxygen nitrating agent and possibly inert gases, and organic compounds such as recycled nitroparaffins) depends on: the quality of the heat exchanges of the reactor; the homogeneity of the reaction mixture and the uniformity of its distribution in the various pipes of the reactor bank, and the nature of the metal which constitutes the reactor bank and the mixer-distributor unit.

In the reactor for nitration of hydrocarbons in the gaseous phase under pressure, made up of a reaction enclosure in which a platelike or pipe bank is in contact with a heat-carrying fluid with great heat exchange capacity, the heat exchanges are assured by a cocurrent or countercurrent circulation, preferable cocurrent, of a heat-carrying fluid able to function satisfactorily at nitration temperatures, for example, between 200° and 450° C. Circulation of the heat-carrying fluid is performed to assure both a sufficient heat exchange at the zone where the reaction is maximal and preheating of reagents to reaction starting temperature, gradual enough to avoid too quick a reaction.

The heat-carrying fluid and its mode of circulation on the outside of the bank are selected so that temperatures of the outside skin of the pipes between the coldest point and the hottest point are kept constant at no more than 25° C. difference.

The size of the pipes of the bank plays an important role in regard to the regular increase of the temperature of the gases during the reaction. A suitable choice of these dimensions makes it possible to control the temperature profile inside the pipes both in the preheating zone and in the reaction zone and in the part corresponding to cooling of the reaction products. In particular, a gradual increase of the temperature in the preheating zone assures stable thermal operating conditions and avoids racing of the reaction which would be reflected by too high a maximum temperature for a correct nitration.

The judicious choice of the ratio between the surface of the pipe bank in contact with the reaction medium and the volume of the reaction enclosure, S/V, has a favorable influence on the regular increase of the temperature during the reaction, when this ratio is between 22 and 425 m$^{-1}$, preferably 50 and 250 m$^{-1}$ and in particular 120 and 250 m$^{-1}$.

The shape and cross section of the pipes (circular, oval or platelike) does not matter as long as it allows a good flow of the gaseous fluid and the heat-carrying fluid assuring the requisite transfer. For this, the inside perimeter of the pipes of the bank should be less than 800 millimeters, preferably less than 500 millimeters, while the thickness of the gas stream should not exceed 150 millimeters, preferable 50 millimeters.

The length of the pipes should be sufficient so that, when the reaction is occuring, the temperature of the gaseous mixture is brought to a value close to the temperature of the heat-carrying fluid, made up for example of molten salts. The minimal length depends on the input temperature in the pipes; if it is slight, the part of the pipes allocated to preheating of the reagents to the temperature when the reaction begins is longer; therefore the total length necessary is greater. Lengths between 8 and 12 meters are perfectly suitable.

The values of the ratios Q/US and Q'/US should be suitably selected so that the reaction can occur under good conditions. Q designates the heat released by the reaction, considering that the latter begins, for example, from 260° C.; Q' designates the total heat exchanged with the heat-carrying fluid, i.e. the sum of the heat given up to the mixture of reaction gases to bring their temperature to 260° C. and the heat given up to the heat-carrying fluid during the reaction and cooling of the gases. U designates the over-all coefficient of the theoretical thermal exchange calculated for reaction gases at the temperature of the heat-carrying fluid and relating to the external surface of the reactional enclosure and S designates the internal exchange surface available in relation to a pipe 12 meters long. These ratios Q/SU and Q'/SU are measured in temperature units and are valid regardless of the size of the pipes. The ratios Q/SU are between 20° and 120° C. and preferably between 40° and 90° C., while the ratios Q'/SU are between 25° and 160° C., preferably 50° and 130° C., and make possible the performance of a nitration reaction under excellent conditions. The over-all exchange coefficient U can advantageously be between 20 and 300 Kcal/hm$^2$° C. and preferably between 30 and 200.

The best heat exchanges are obtained, on the one hand, from the choice of a suitable heat-carrying fluid, selected from mixtures of molten salts such as nitrites and nitrates of alkali metals; and, on the other hand, from an effective circulation of the heat-carrying fluid, characterized by a maximal reduction of the zones of least heat transfer quality. An excellent heat transfer is obtained by a crosswise circulation of the heat-carrying fluid in relation to the bank.

The tubular or platelike bank is equipped with segmented, disk or ring type baffles, distributed irregularly along the entire axis of the bank; the distances separating two baffles being minimal at right angles with the zone where the nitration reaction occurs.

Further, distribution of the reaction gases at the input of the pipe bank, the design of the latter and the circulation of the heat-carrying fluid are such that preferably the reaction will have the greatest possible symmetry around an axis parallel to the pipes. The bank does or does not comprise pipes in the central part.

The reactor is fed by a mixer-distributor unit intended, on the one hand, to assure a homogeneous mixing of the group of reagents and, on the other hand, to distribute this homogeous mixture in a regular manner between the various pipes.

The mixture assures a homogeneous mixture of the reaction fluids so that the maximum divergence of concentration at any point of the distributor does not exceed 3%, preferably 1%.

Obtaining nitration products with good yields also depends on regular maintenance of deliveries, therefore on the dwell time in the various pipes of the bank, these latter having to be charged as identically as possible. The mixer-distributor is equipped, for this purpose, with a suitable static device, which regularly distributes the infeed to the pipes of the bank so that the maximal load difference between the heaviest loaded pipe and the least loaded does not exceed 3%.

The mixer-distributor can be designed with or without circulation of the heat-carrying fluid over all or part of the mixing and distribution zones, the heat-carrying fluid never having to be in direct contact with the gases.

Mixing and distribution should occur in a sufficiently short time, at most 0.5 second, and preferably less than 0.1 second. The velocities of the gases in the mixer-distributor apparatus advantageously remain between 3 and 50 meters per second.

The mixer-distributor for the various pipes of the bank, combining the technology of dynamic and static mixing, is provided with a succession of widenings and narrowings of gas passage sections, in particular a considerable narrowing of the passage section at right angles with each pipe of the bank; this restriction makes possible a better distribution of the gases between each pipe.

The pipe bank and the mixer-distributor unit should be made of metals able to resist corrosions caused by nitrating agent and resistant to the heat-carrying fluid. This metal should further be selected so that it does not have the effect of favoring oxidation reactions that compete with the nitration. In particular, certain austenitic stainless steels with nickel-chromium give total satisfaction. They are of the Z 12 CNS 25-20, Z 3 CN 18-10, A 310 A, A 1S1 310S types and the Inconels, Inconel 600, norm AFNOR ZNCSE 72-14 or ZNC Fe 72-14 (AFNOR standard).

Composition of said steels:

| | | |
|---|---|---|
| Z3 C N 18-10: | C max. 0.035; | Cr 18.5; Ni 10.5 |
| Z 12 CNS 25-20 AISI 310 S. | C max. 0.10; | Cr 25; Ni 20 |
| Inconel 60: | C max. 0.2; Fe 6-10; Mn<1. | Cr 14-17; Ni ≦ 72; Cu < 0.7; Si < 0.5; |

The reactor of the invention is characterized by the structural arrangements that will be cited below and the parameters relating to the temperature of the pipe skin, to the diameter of the pipes, to the ratios S/V, Q/S, QUS and U, which are set forth below.

In FIG. 1, the reaction mixture is introduced through the lower part of vertical pipe bank (1) and vertical lines (2) represent some pipes in which the reaction mixture circulates upwardly.

The heat-carrying fluid circulates outside the pipes (2) in the same direction, cocurrent with the gases. The heat-carrying fluid is introduced and removed through inlet and outlet pipes (3) and (4). Circulation of the heat-carrying fluid is controlled by the arrangement of baffles which extend partly across the reactor, hereinafter segmented type baffles (5), distributed irregularly and with minimal distance therebetween at right angles to the length of the reactor, i.e. in the central part of the pipe between B and B'. (The intervals in dotted lines C and C' correspond to the parts of the pipe (not shown) in the height of 12 meters).

Figure 2:
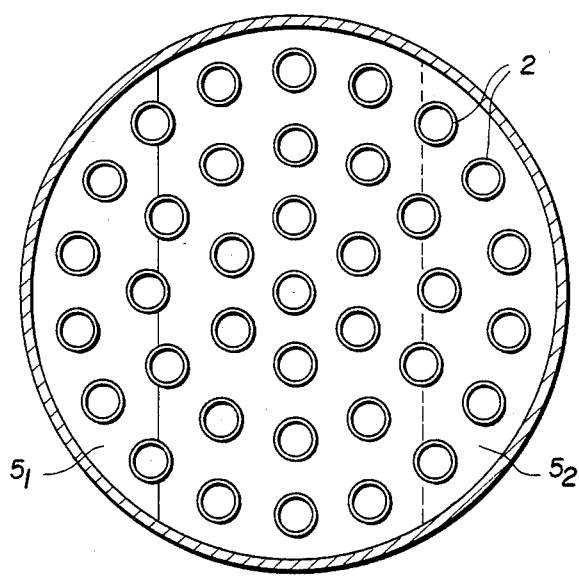
FIG. 2 is a cross-section taken at 2—2 in FIG. 1 showing the distribution of the 37 pipes of the reactor embodiment.

FIG. 2 corresponds to a cross section with distribution of 37 pipes (2) at 2—2 of FIG. 1. Segmented baffles $5_1$ and $5_2$ can be seen in this figure.

Figure 3:
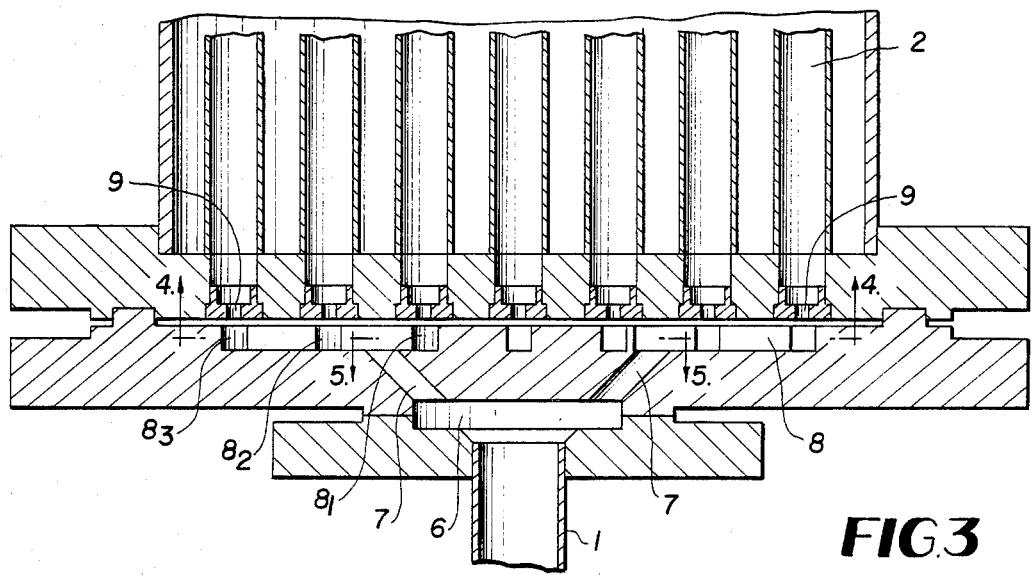
FIG. 3 is a section of the lower part of the pipe bank.
Figure 4:
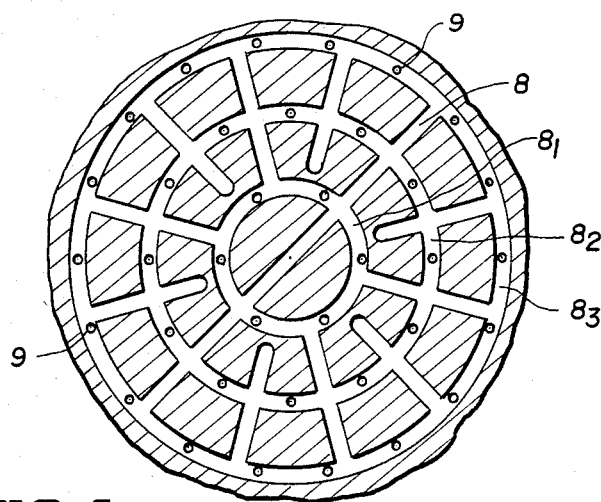
FIG. 4 is a cross-section taken at 4—4 in FIG. 3 of the pipe bank showing the distribution of the reaction mixture in the pipes.
Figure 5:
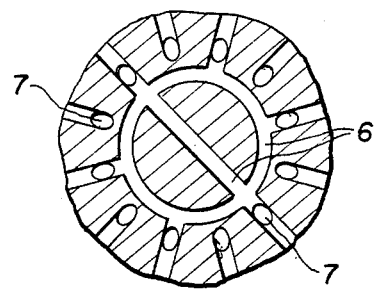
FIG. 5 is a cross-section taken at 5—5 in FIG. 3 showing the distribution of the reaction mixture.

FIGS. 3, 4 and 5 each show distribution of the gases in the reactor system.

The reaction gas mixer is not shown in FIG. 3. At the output of the mixer, the gases arrive by conduit (1) at the base of the divider-distributor device that causes accelerations and decelerations in the distribution zone at (6) (FIGS. 3 and 5). The gases enter a deceleration zone from which radiate conduits (7) in which the velocity of the gases is accelerated. At this level, the gases distributed by conduits 7 are distributed as shown in FIG. 4 along section 4—4 by radial distribution channels 8 and three circular distribution channels $8_1$, $8_2$, $8_3$; in this zone, there is deceleration. The distribution channels are at the base of the pipes and lie in their axes. Then the gases leaving the channels are forced toward a calibrated passage 9 at the input and in the axis of the pipes, which involves a final acceleration of the gases at the input of the pipes. A tube bank injector is utilized to assure homogeneous mixing of all reaction fluids.

EXAMPLE I

A prototype reactor for the nitration of hydrocarbons in the gaseous phase under pressure is made up of a bank of 37 pipes.

The pipe bank is made up of 37 stainless steel pipes of Z 12 CNS 25-20 (CO 10, Cr 25, Ni 20) 12 meters long, with an inside and outside diameter of 21.7 and 26.9 millimeters distributed at a triangular pitch of 46 millimeters. It is possible to block a certain number of the pipes to use n pipes of the bank, n being selected to be about 30, depending on the desired operating conditions.

The ratio between the inside surface of the pipes and the inside volume of the bank is 184 $m^{-1}$.

Heat exchanges are assured by a circulation cocurrent with the heat-carrying fluid made up of a mixture of molten salts: 40% sodium nitrite ($NaNO_2$), 7% sodium nitrate ($NaNO_3$) and 53% potassium nitrate ($KNO_3$).

Segmented baffles are arranged irregularly inside the pipes to allow a variation of a ratio of 1 to 3 of the heat-carrying fluid.

The ratios Q/SU and Q'/SU can vary form 55 to 80 for Q/SU and 70-105 for Q'/SU while the ratio between the heat to be evacuated can vary between 3000 and 6000 Kcal/hm².

The reaction gases are mixed in a double pipe mixer provided with helicoidal wings assuring a homogeneous mixing of such quality that the maximal variation of concentration at any point of the distributor does not exceed 3%, in a period of 0.03 to 0.04 seconds for velocities of 4 to 25 meters per second.

The mixture of reaction gases then circulate in a distributor-divider where it is subjected to a succession of decelerations and accelerations during which the velocities are kept in an interval of 2 to 25 meters per second. Intake of the reaction mixture in each pipe of the bank occurs through a calibrated orifice that causes a considerable load loss and gas velocities increasing from 15 to 30 meters/second, which makes possible a good distribution of the gas mixture between the various pipes of the bank: the maximal divergence between the deliveries at the input of each pipe does not exceed 3%.

By a device with stationary thermocouples and one with a mobile thermocouple, the thermal profile of the temperatures of the reaction enclosure is known; this knowledge makes it possible to vary the parameters of the reaction such as Q/SU, U, contact time, delivery of the heat-carrying fluid, while controlling the evolution of the nitration.

1a. Nitration in a reactor having 36 pipes in operation

Temperatures of the molten salts
= input: 299° C.
= output: 300° C.

Pressure of the gases in the mixer-distributor: 8.8 Kg/cm² effective

TABLE I

|  | REACTOR INPUT kg/h | REACTOR OUTPUT kg/h |
|---|---|---|
| $C_3H_8$ | 380.78 | 335.79 |
| $C_2H_6$ | 1.74 | 1.73 |
| $C_4H_{10}$ | 3.76 | 2.76 |
| $NO_2$ | 102.08 | |
| $O_2$ | 20.64 | |
| $N_2$ | 71.16 | 72. |
| CO | | 9.24 |
| $CO_2$ | | 15.41 |
| NO | | 38.78 |
| $H_2O$ | | 32.05 |
| methanol $CH_3OH$ | | 0.05 |
| acetaldehyde $CH_3CHO$ | | 2.97 |
| ethanol $C_2H_5OH$ | | — |
| acetonitrile $CH_3CN$ | | 1.86 |
| acetone $(CH_3)_2CO$ | | 4.24 |
| propionitrile $C_2H_5CN$ | | .56 |
| nitromethane $CH_3NO_2$ | | 21.43 |
| Nitroethane $C_2H_5NO_2$ | | 5.32 |
| 2 Nitro-propane $(CH_3)CHNO_2$ | | 25.12 |
| 1 Nitro-propane $C_3H_7NO_2$ | | 10.57 |
| Nitrous acid $HNO_2$ | | .98 |
| Nitric acid $HNO_3$ | | .51 |

Dwell time calculated as follows: 8.5 seconds dwell time for a constant gas delivery equal to voluminal delivery at the input of the pipes, under a constant pressure equal to the input pressure and a constant temperature equal to the average temperature of the heat-carrying fluid.

| | |
|---|---|
| Q = heat released during reaction (going from 260° C.) | 120 172 Kcal/h |
| heat supplied to reagents to bring them to 260° C. | 31 972 Kcal/h |
| Q' = total heat exchange between the gases and the heat-carrying fluid | 152 144 Kcal/h |
| Q/S = 4005 Kcal/hm² | |
| | Q'/S = 5.166 Kcal/hm² |
| Q/US = 63° C. | |
| U = 64.6 Kcal/hm²°C. | Q'/US = 80° C. |

Figure 6:
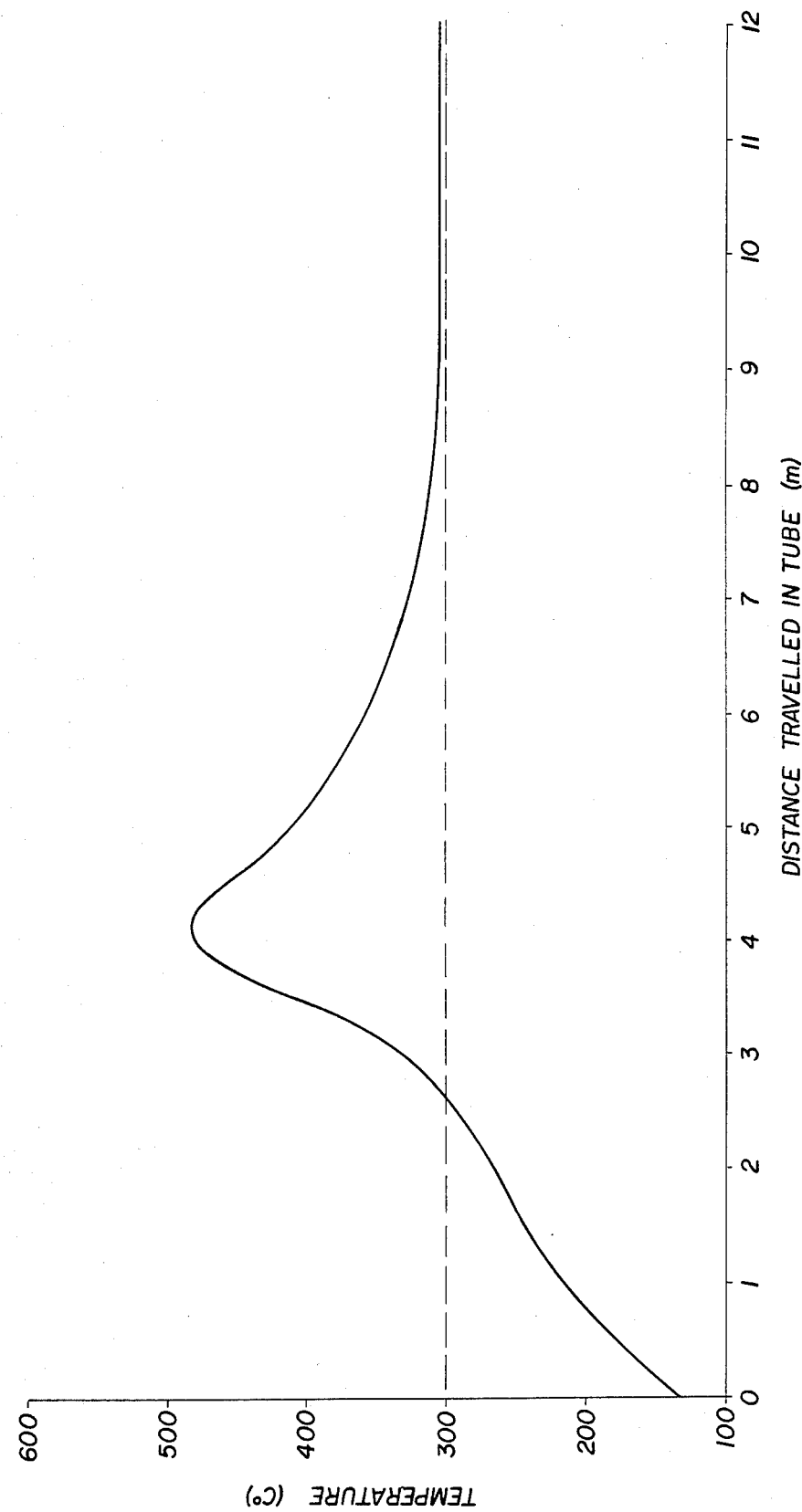
FIG. 6 is a graph showing the temperature variation in the reactor tubes for the reaction conditions described in Example 1, infra.

The profile of the temperature in the reactor pipes appears on the curve of FIG. 6, the distance traveled in the tube by the reaction mixture expressed in meters is on the x-axis and the temperatures in ° C. on the y-axis.

1b. Nitration in a 36-pipe reactor

Temperature of molten salts
= input: 329° C.
= output: 331° C.

Pressure input pipes: 9.7 kg/cm² effective

TABLE II

|  | INPUT KG/H | OUTPUT KG/H |
|---|---|---|
| $C_3H_8$ | 417.21 | 377.67 |
| $C_2H_6$ | 1.43 | 1.42 |
| $C_4H_{10}$ | 4.49 | 2.56 |
| $NO_2$ | 121.99 |  |
| $O_2$ | 28.98 |  |
| $N_2$ | 96.88 | 95.47 |
| CO |  | 8.92 |
| $CO_2$ | .51 | 17.35 |
| NO |  | 68.32 |
| $H_2O$ |  | 42.68 |
| $CH_3OH$ |  | .51 |
| $CH_3CHO$ |  | 11.65 |
| $C_2H_5OH$ |  | — |
| $CH_3CN$ |  | .03 |
| $(CH_3)_2CO$ |  | 3.10 |
| $C_2H_5CN$ |  | — |
| $CH_3NO_2$ | .11 | 18.84 |
| $C_2H_5NO_2$ | 7.92 | 11.92 |
| $(CH_3)_2CHNO_2$ | 46.82 | 55.80 |
| $C_3H_7NO_2$ | 3.56 | 13.04 |
| $HNO_2$ |  | .42 |
| $HNO_3$ |  | 2.96 |

Dwell time according to definition example I=6.5 seconds

Q = 132 850 Kcal/h
Q' = 174 850 Kcal/h
Q/US = 49° C.
Q'/US = 47.5° C.
Q/S = 4514 Kcal/hm²
Q'/S = 5940 Kcal/hm²
U = 92 Kcal/hm²°C.

EXAMPLE II

An industrial reactor for the nitration of hydrocarbons in the gaseous phase under pressure is made up of a bank of 1156 pipes and functions under the same principles, which define a gas distribution system.

The pipe bank of this reactor is made up of 1156 pipes of stainless steel of the type Z 12 CNS 25-20(CO 10,Cr, 25,Ni 20, silicon≦1) or AlSi 310, with inside and outside diameters of 22.10 and 25.4 millimeters, and 12 meters long. The ratio between the inside surface of the pipes of the bank and the inside volume of the bank is 181 m⁻¹.

For nitration of an ethane-propane mixture, the ratios Q/SU and Q'/SU can vary between 45 and 60° C. for Q/SU and between 55° and 80° C. for Q'/SU.

As in the preceding reactor the heat exchanges are assured by a cocurrent circulation of a mixture of molten salts with 40% by mass of $NaNO_2$, 7% $NaNO_3$ and 53% $KNO_3$.

The pipe bank exhibits a symmetry of revolution in relation to an axis parallel to the pipes, the baffles placed on the inside of the pipe bank are of the disk type and rings are distributed irregularly along the axis of the bank, the distances separating two baffles being minimal at right angles with the zone where the reaction occurs.

The mixture of reaction gases, the distribution-division of the mixture, its intake, the thermal control of the temperatures of the reaction enclosure are achieved under the same conditions as in Example 1.

This type of reactor is suited to an industrial scale of nitration of any hydrocarbon or mixture of saturated hydrocarbons lower than $C_5$, and for example nitration of a mixture of ethane and propane, according to the following balance.

Input pressure=11 effective bars
Temperature of the molten salts: 330° C.
Input temperature of the gases: 150° C./output temperature: 340° C.

TABLE III

|  | INPUT PIPES KG/H | OUTPUT PIPES KG/H |
|---|---|---|
| $C_2H_6$ | 6554.79 | 6176.43 |
| $C_3H_8$ | 6569.38 | 5733.33 |
| $C_4H_{10}$ | 1.06 | .96 |
| iso $C_4H_{10}$ | 5.01 | 4.00 |
| CO | 1813.41 | 2176.13 |
| $CO_2$ | 3864.15 | 4672.09 |
| $N_2$ | 41.35 | 41.35 |
| $O_2$ | 734.44 |  |
| NO | 38.66 | 1985.47 |
| $NO_2$ | 3958.94 |  |
| $N_2O_4$ |  |  |
| $N_2O$ | 67.86 | 67.86 |
| $H_2O$ | 72.35 | 991.36 |
| Nitromethane | .24 | 585.71 |
| Nitroethane | 55.77 | 475.16 |
| 1 Nitro-Propane | 149.98 | 352.07 |
| 2 Nitro-Propane | 874.79 | 929.95 |
| 2 Nitro-Butane | .08 | 1.14 |
| Methanol |  | 52.12 |
| Ethanol |  | 15.20 |
| Formaldehyde |  | 12.31 |
| Acetaldehyde |  | 242.06 |
| Acetone |  | 106.38 |
| Formic acid |  | .46 |
| Acetic acid |  | 6.08 |
| Acetonitrile |  | 30.39 |
| Propionitrile |  | 1.98 |
| $CHNO_2$ |  | 29.33 |
| $HNO_3$ |  | 106.37 |

From the foregoing it will be evident that an improved nitrating reactor, having the advantages described above, has been designed and constructed.

It will be obvious to those skilled in the art, that various changes may be made without departing from the scope of the invention, and the invention is not to be considered limited to what is specifically described in the specification.

What is claimed is:

1. In a reactor for nitration in the gaseous phase under pressure of the type including a reaction enclosure having upper and lower ends, a conduit for introducing reaction gases into said enclosure, means for introducing heat-carrying fluids, means for extracting the heat-carrying fluids, and a bank of tubes contained within the enclosure, the improvement comprising;
   means for distributing the introduced reaction gases to said tubes, said distributing means being disposed between said conduit and said tubes and defining means for successively decelerating and accelerating said introduced gases, said successively decelerating and accelerating means including first channel means disposed at the base of said tubes, said first channel means comprising a plurality of concentric circular deceleration channels disposed substantially normal to said tubes, and acceleration passages connected between said deceleration channels and said tubes, and second channel means extending from said conduit through a deceleration chamber to acceleration channels radiating at an angle away from said deceleration chamber toward, and interconnecting, said first channel means, each of first channel means and said second channel means successively decelerating and accelerating said gases, whereby upon passing through said first and second channel means from said conduit, said gases become homogenously mixed prior to being distributed to said tubes.

2. The improvement of claim 1 wherein:
said acceleration passages are calibrated, and
said second channel means comprises a deceleration channel connecting said conduit with said deceleration chamber, and having a larger cross-sectional area at the one end joining said deceleration chamber than at the other end joining said conduit.

3. The improvement of claim 1 wherein
said deceleration channels are interconnected by a plurality of radially extending interconnecting channels the latter being substantially normal to said deceleration channels and said tubes.

4. A reactor for nitration in the gaseous phase under pressure comprising a reaction enclosure having an upper end and a lower end and containing a vertical plate bank of tubes, a conduit for the introduction of reaction gases at the lower end of the reaction enclosure, means for introducing and extracting heat-carrying fluids, wherein the plate bank of tubes is equipped with segmented compartments separated by disc or ring-type partitions irregularly distributed along the length of the bank; the distances separating two partitions beng minimal in the central portion of the bank in a region defining a reaction zone, wherein the reactor includes at said lower end means for distributing said reaction gases to different tubes of the bank, said distributing means being disposed between said conduit and said tubes and defining means for successively decelerating and accelerating the introduced gases, said successively decelerating and accelerating means including first channel means disposed at the base of said tubes, said first channel means comprising a plurality of concentric circular deceleration channels disposed substantially normal to said tubes, and acceleration passages connected between said deceleration channels and said tubes, and second channel means extending from said conduit through a deceleration chamber to acceleration channels radiating at an angle away from said deceleration chamber toward, and interconnecting, said first channel means, each of said first channel means and said second channel means successively decelerating and accelerating said gases, whereby upon passing through said first and second channel means from said conduit, said gases become homogenously mixed prior to being distributed to said tubes.

* * * * *